(12) United States Patent
Haffner et al.

(10) Patent No.: US 7,650,050 B2
(45) Date of Patent: Jan. 19, 2010

(54) OPTICAL SENSOR DEVICE FOR LOCAL ANALYSIS OF A COMBUSTION PROCESS IN A COMBUSTOR OF A THERMAL POWER PLANT

(75) Inventors: Ken Yves Haffner, Baden (CH); Tony Kaiser, Bülach (CH); Valery Shklover, Zürich (CH)

(73) Assignee: ALSTOM Technology Ltd., Baden (CH)

( * ) Notice: Subject to any disclaimer, the term of this patent is extended or adjusted under 35 U.S.C. 154(b) by 0 days.

(21) Appl. No.: 11/275,074

(22) Filed: Dec. 8, 2005

(65) Prior Publication Data
US 2007/0133921 A1 Jun. 14, 2007

(51) Int. Cl.
G02B 6/00 (2006.01)
G01J 1/56 (2006.01)
G01B 11/14 (2006.01)

(52) U.S. Cl. ............... 385/12; 250/231.19; 356/615
(58) Field of Classification Search .............. 385/12; 250/231.19; 356/615; 422/83
See application file for complete search history.

(56) References Cited

U.S. PATENT DOCUMENTS

| | | | | |
|---|---|---|---|---|
| 4,756,684 A * | 7/1988 | Nishikawa et al. | ............ | 431/79 |
| 4,764,343 A * | 8/1988 | Nyberg | ............ | 422/83 |
| 4,932,262 A * | 6/1990 | Wlodarczyk | ............ | 73/705 |
| 5,139,611 A | 8/1992 | Pusey et al. | ............ | 359/885 |
| 5,550,375 A | 8/1996 | Peters et al. | ............ | 250/343 |
| 6,180,239 B1 | 1/2001 | Whitesides et al. | ...... | 428/411.1 |
| 6,304,364 B1 | 10/2001 | Qin et al. | ............ | 359/291 |
| 6,355,198 B1 | 3/2002 | Kim et al. | ............ | 264/259 |
| 6,518,168 B1 | 2/2003 | Clem et al. | ............ | 438/623 |

FOREIGN PATENT DOCUMENTS

| | | | |
|---|---|---|---|
| JP | 08327053 A | * | 12/1996 |
| JP | 11118145 A | * | 4/1999 |
| JP | 2005227187 A | * | 8/2005 |

OTHER PUBLICATIONS

Bellet, D., et al., "Controlled Drying: The Key to Better Quality Porous Semiconductors," Adv. Mater. 1998;10(6):487-490, Wiley-VCH, Weinheim, Germany, no month.
Bendiab, N., et al., "Structural determination of iodine localization in single-walled carbon nanotube bundles by diffraction methods," Phys. Rev. B 2004;69;195415-1-195415-8; American Physical Society, College Park, MD, U.S.A., no month.

(Continued)

*Primary Examiner*—Hemang Sanghavi
(74) *Attorney, Agent, or Firm*—Cermak Kenealy Vaidya & Nakajima LLP; Adam J. Cermak

(57) ABSTRACT

An optical sensor device for local analysis of a combustion process in a combustor of a thermal power plant, in particular a gas turbine plant, includes at least one wavelength selective optical element exposed directly or indirectly to hot combustion gases being produced by said combustion process, the optical element including an array of nano- and/or microcrystalline fibres which are created by shear flow crystallization.

26 Claims, 16 Drawing Sheets

OTHER PUBLICATIONS

Braginsky, L., et al., "High-temperature phonon thermal conductivity of nanostructures," Phys. Rev. B 2002;66:134203-1-134203-9, American Physical Society, College Park, MD, U.S.A., no month.

Braginsky, L., et al., "High-temperature thermal conductivity of porous Al2O3 nanostructures," Phys. Rev. B 2004;70:134201-1-134201-7, American Physical Society, College Park, MD, U.S.A., no month.

Butler, M. A., et al., "The Quantification of Different Forms of Cristobalite in Devitrified Alumino-Silicate Ceramic Fibres," J. Appl. Cryst. 1997;30:467-475, International Union of Crystallography, Great Britain, no month.

Cambedouzou, J., et al., "Raman spectroscopy of iodine-doped double-walled carbon nanotubes," Phys. Rev. B 2004;69:235422-1-235422-6, American Physical Society, College Park, MD, U.S.A., no month.

Chakarian, V., et al., "The adsorption of I2 on Si(111)-7X7 studied by soft X-ray photoemission," Surf. Sci. 1993;296:383-392, Elsevier, B.V., Amsterdam, Netherlands, no month.

Choi, W. B., et al., "Fully sealed, high-brightness carbon-nanotube field-emission display," Appl. Phys. Lett. 1999;75(20):3129-3131, The American Institute of Physics, Argonne, IL, U.S.A., Nov. 1999.

De Hosson, J. T., et al., "Nanosized Metal Clusters: Challenges and Opportunities," JOM Jan. 2004;40-45, The Mineral, Metals and Material Society, Warrendale, PA, U.S.A.

Elliott, G. S., et al., "Molecular filtered Rayleigh scattering applied to combustion," Meas. Sci. Technol. 2001;12:452-466, IOP Publishing, Ltd., United Kingdom, no month, 2001.

Estermann, M., et al., "A high-temperature furnace for X-ray diffraction with directly machined a-Al2O3 ceramic parts," J. Appl. Cryst. 1999;32:833-836, International Union of Crystallography, Great Britain, no month.

Göthelid, M., et al., "An ordered layer of molecular iodine on Ge(100) 2X1," Surface Science 2004;556:203-212, Elsevier, B.V., Amsterdam, Netherlands, no month.

Grigorian, L., et al., "Reversible Intercalation of Charged Iodine Chains into Carbon Nanotube Ropes," Phys. Rev. Lett. 1998;80(25):5560-5563, The American Physical Society, Argonne, IL, U.S.A., Jun. 1998.

Hu, M. Z.-C., et al., "Nanocrystallization and Phase Transformation in Monodispersed Ultrafine Zirconia Particles from Various Homogeneous Precipitation Methods," J. Am. Ceram. Soc. 1999;82(9):2313-2320, Blackwell Publishing, Inc., Malden, MA, U.S.A., no month.

Huang, Y., et al., "Directed Assembly of One-Dimensional Nanostructures into Functional Networks," Science 2001;291:630-633, Science/AAAS, Washington, D.C., U.S.A., Jan. 2001.

Li, Z., et al., "Inorganic Electride: Theoretical Study on Structural and Electronic Properties," J. Am. Chem. Soc. 2003;125:6050-6051, The American Chemical Society, Washington, D.C., U.S.A., no month.

Lu, Y., et al., "Growth of Large Crystals of Monodispersed Spherical Colloids in Fluidic Cells Fabricated Using Non-photolithographic Methods," Langmuir 2001;17:6344-6350, The American Chemical Society, Washington, D.C., U.S.A., no month.

Most, D., et al., "Simultaneous two-dimensional flow velocity and gas temperature measurements by use of a combined particle image velocimetry and filtered Rayleigh scattering technique," Appl. Optics 2001;40(30):5379-5387, The Optical Society of America, Washington D.C., U.S.A., Oct. 2001.

Padmore, H. A., et al., "Grazing-Incidence Monochromators for Third-Generation Synchrotron Radiation Sources," in Experimental Methods in the Physical Sciences, Vacuum Ultraviolet Spectroscopy II, vol. 32, Edited by J. A. R. Samson and D. L. Ederer, Academic Press 1998, pp. 21-54, no month.

Prasad, B. L. V., et al., "Intercalated nanographite: Structure and electronic properties," Phys. Rev. B;64:235407-1-235407-10, The American Physical Society, College Park, MD, U.S.A., no month, 2001.

Shimoda, H., et al., "Self-Assembly of Carbon Nanotubes," Adv. Mater. 2002;14(12):899-901, Wiley-VCH, Weinheim, Germany, Jun. 2002.

Shklover, V., "Formation of Aligned Microfiber Arrays via Self-Assembling SiO2 Nanocolloids. Change of Microfiber Structure during Annealing," Chem. Mater. 2005;17:608-614, The American Chemical Society, Washington, D.C., U.S.A., no month.

Song, M. K., et al., "Disproportionation of an Element in a Zeolite. II. Crystal Structure of an Iodine Sorption Complex of Dehydrated Fully Cd2+-Exchanged Zeolite X Containing n-I5-as I—I3+-I- and Square cyclo-I42+," J. Phys. Chem. B 2003;107:10709-10714, The American Chemical Society, Washington, D.C., U.S.A., no month.

Wei, Y., et al., "Stability of carbon nanotubes under electric field studied by scanning electron microscopy," Appl. Phys. Lett. 2001;79(27):4527-4529, The American Institute of Physics, Inc., College Park, MD, U.S.A., Dec. 2001.

Xia, Y., et al., "Fabrication of Three-Dimensional Photonic Crystals for Use in the Spectral Region from Ultraviolet to Near-Infrared," J. Lightwave Technol. 1999;17(11):1956-1962, IEEE Lasers & Electro-Optics Society, Piscataway, NJ, U.S.A., Nov. 1999.

Xia, Y., et al., "Monodispersed Colloidal Spheres: Old Materials with New Applications," Adv. Mat. 2000;12(10):693-713, Wiley-VCH, Weinheim, Germany, no month.

Xia, Y., et al., "Building Complex Structures from Monodisperse Spherical Colloids," Aust. J. Chem. 2001;54:287-290, CSIRO Publishing, Victoria, Australia, no month.

Yin, Y., et al., "Template-Assisted Self-Assembly: A Practical Route to Complex Aggregates of Monodispersed Colloids with Well-Defined Sizes, Shapes, and Structures," J. Am. Chem. Soc. 2001;123:8718-8729, The American Chemical Society, Washington, D.C., U.S.A., no month.

Zhu, W., et al., "Large current density from carbon nanotube field emitters," Appl. Phys. Lett. 1999;75(6):873-875, The American Institute of Physics, Inc., College Park, MD, U.S.A., Aug. 1999.

Shklover, V., "Formation of Aligned Microfiber Arrays via Self-Assembling SiO2 Nanocolloids. Change of Microfiber Structure during Annealing," Chem. Mater. 2005, 608-614, 17(3), no month.

International Search Report for PCT Patent App. No. PCT/EP2005/055280 (Feb. 9, 2006).

* cited by examiner

OPTICAL SENSOR DEVICE FOR LOCAL ANALYSIS OF A COMBUSTION PROCESS IN A COMBUSTOR OF A THERMAL POWER PLANT

BACKGROUND OF THE INVENTION

1. Field of the Invention

The invention relates to an optical sensor device for local analysis of a combustion process in a combustor of a thermal power plant, in particular a gas turbine plant.

2. Brief Description of the Related Art

An important aspect of operating highly advanced thermal power plants, especially gas turbine plants, concerns the quality of combustion and the generation of hot gases for powering turbine stages. It is a known fact that from analyzing hot gases shortly after the combustion process and before entering the turbine stages, valuable information about burner quality and emission values can be derived for online optimizing procedures concerning the combustion process.

Due to the very high temperature level inside a combustor the choice of available sensor systems withstanding such temperatures beyond 1000° C. is very limited. No durable sensor system is presently known which is applicable and reliable for measuring burner parameters in a very direct manner. Optical remote sensing systems are known which, however, have to be secured against the high temperatures inside the combustor. This requirement confines reliability and place of installation.

One of the inventors hereof, Valery Shklover, discussed some aspects of self-assembling spherical colloidal $SiO_2$ nanoparticles in Shklover, Valery, Formation of Aligned Microfiber Arrays via Self-Assembling SiO2 Nanocolloids. Change of Microfiber Structure during Annealing, 17 Chem. Mater. 608-614 (American Chemical Society, 8 Jan. 2005), the entirety of which is incorporated by reference herein.

SUMMARY OF THE INVENTION

It is therefore an aspect of the invention to provide a sensor system for local analysis of a combustion process in a combustor of a thermal power plant, in particular a gas turbine plant which withstands the high temperature level inside a combustor and which yields credible burner information, especially information of hot gas consistency and physical behavior like temperature and pressure. The sensor device preferably is of simple construction and inexpensive fabrication An inventive sensor embodying principles of the present invention is described, with preferable features, in the following description.

The inventive sensor is an optical sensor device useful for local analysis of a combustion process in a combustor of a thermal power plant, in particular a gas turbine plant providing at least one wavelength selective optical element exposed directly or indirectly to hot combustion gases being produced by the combustion process.

The optical element provides an array of nano- and/or microcrystalline fibers which are thermally and chemically resistant and created by use of shear flow crystallization. For measurement purpose a light source is provided emanating a light beam favorably of a broad bandwidth for passing through the optical element directed onto a mirror which is arranged oppositely to the light source in respect to the optical element having a mirror surface onto which the light beam is reflected at least partly so that at least a reflected light beam fraction passes the optical element in the opposite direction. A detector is positioned at the same site of the optical element as the light source for detecting the reflected light.

Since the mirror surface and the optical element are arranged apart by distance and the space between the components is flooded with hot gas, twice the distance between the optical element and the mirror surface therefore serves as an absorption length for the propagating light beam in the space.

The optical element is produced by means of shear flow crystallization which is explained in the following broadly and provides the function of a wavelength selective filter, like a notch or Bandwidth-filter. The wavelength selectivity has to be chosen in dependence on the absorption bands of atoms or molecules of interests which shall be measured along the aforementioned absorption length. The nano- and/or microcrystalline fibers which are created as a so called primary array in the course of the shear flow crystallization process are made of high temperature resistant material like metal oxides, metal or other inorganic nanoparticles, deposited onto an amorphous, polycrystalline or single crystalline flat or curvature support using shear-flow crystallization methods under distinct crystallization conditions and post-crystallization thermal treatment, leading to closely packed and distinct crystallographically rational orientation of the crystal packing of microfibers relative to their external faces and leading to distinct orientation of the microfibers relative to crystallization cell geometry.

The starting suspensions of the shear-flow crystallization can be monodisperse or can have different particle size. The substrates' surfaces can be flat or possess curvature. The pre-sintering process is important for formation of nanopatterns of required dimensionality. The nano- or microarray thickness and shape can be controlled by crystallization cell design. Controlled heat treatment can be applied for controlling the coalescence of nanoparticles and for creating the crystallinity of the low-dimensional nano- or microarrays, providing a gradient of properties across the micro- or nanoarrays, or across the article, built of micro- or nanoarray. The low-dimensional nano- or microarrays with graded properties can be fabricated. The possible applications include waveguides, monochromators, focusing devices, tunable transmitting filters, mono- and multilayered mirrors. One of the applications is the use of patterned photonic microfiber arrays as a pattern for design of an array of aligned nanotube array with adsorbed molecular iodine or other material for use as part of filter system in filtered Rayleigh scattering (FRS) laser diagnostic or other sensors. Suggested fabrication method belongs to enabling technology for the inventive applications in gas turbine: broad-band and narrow-band filters for suppression of absorption from molecules in distinct spectrum regions (UV, visible, IR), selective band photonic defect-induced band-pass filters, mesoporous framework structures for FRS super-narrow notch filters, molecular super-narrow-band notch filters based on, for example, molecular iodine encapsulated inside of mesoporous framework solids. Particularly promising for local gas turbine diagnostics (temperature, pressure, $NO_x$ pollutant emissions, CO emissions, unburned hydrocarbons, volatile organic compounds, nitrous oxides, sulphur oxides) is the application of new nanoarrays in nanocrystalline photonic filters at high temperature.

This invention therefore uses for the optical element one-dimensional arrays as primary arrays (nano- or microfibers) and, built of these one-dimensional arrays, two-dimensional nano- and microarrays (secondary arrays) of controlled shape, thickness and microstructure on the planar and curvature surfaces for applications in patterning, in visible and UV optics as mono- or multilayered filters. The inventive sensor can also be applicable as chemical or biological sensor in addition to local sensor systems in a gas turbines for local diagnostic purposes. Application in local diagnostic systems in gas turbines concerns use of primary 2D arrays as patterns for alignment of nanotubes doped with molecular iodine or other materials to ensure tunable ultra-thin notch filter properties for application in filtered Rayleigh scattering (FRS) laser diagnostic.

Basically, methods of nanotechnology are extensively used for creating new materials for optics, microelectronics and sensorics. Here the shear-flow crystallization of organic, metal oxide and metallic nanocolloids is used for obtaining different functional structures for the inventive application. Waveguides are important components of sensors and switches and composed of a core, surrounding by a cladding, which acts as a guide of electromagnetic radiation. The mechanism of wave guiding is total internal reflection of the radiation within the core.

Generally, creating a waveguide requires changing the refractive index in the device.

By using flexible substrates carrying many waveguides, flexible waveguides could be fabricated. In the waveguides, the core and cladding can be formed of the same material, for example of the polymer with different degree of polymerization, which depend on the curing time. The refraction index contrast in the micro- or nanoarrays, described herein, is created by the ordered alignment of one-dimensional arrays, controlled by the drying process.

BRIEF DESCRIPTION OF THE DRAWINGS

The present invention is made more apparent, by way of example without the intention of limiting the spirit or scope of the inventive idea, using preferred embodiments with reference to the accompanying drawings, in which.

DETAILED DESCRIPTION OF EXEMPLARY EMBODIMENTS

Figure 1:
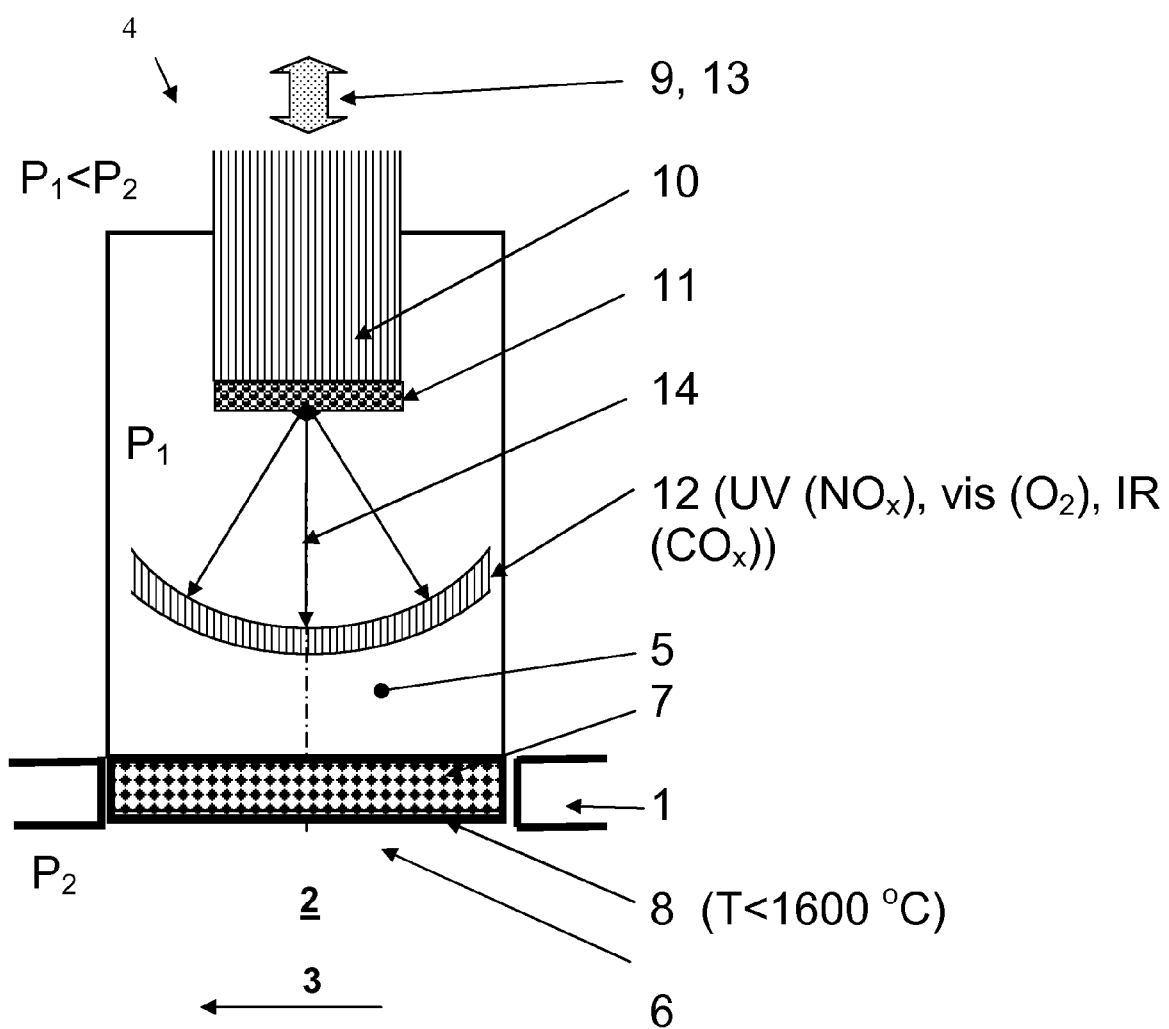
FIG. 1 High-temperature stable gas sensor for local combustion gas detection

FIG. 1 shows a temperature stable gas sensor for local combustion gas detection which is insertable in the wall 1 of a combustion chamber of a gas turbine arrangement. The wall 1 encloses the combustion chamber 2 in which hot gases 3 are produced in a combustion process. The optical sensor 4 is positioned at a location downstream of the flame of the combustor. At this location an opening 6 in the combustors wall 1 is provided at which a measuring volume is encapsulated like a little chamber 5 which is positioned outside of the wall bordering the combustion chamber. The opening 6 is covered with a high temperature resistant selective porous membrane 7 through which selective constituents of hot gases can pass. To enhance the temperature resistance of the porous membrane 7 a protection coating 8 covers the porous membrane 7 at a side facing the combustion chamber which withstands temperatures up to 1600° C.

Inside the little chamber 5 the optical sensor 4 is arranged for detecting important parameters of the combustion process, like temperature, pressure, $NO_x$ pollutant emissions, CO emissions, unburned hydrocarbons, volatile organic compounds, nitrous oxides and/or sulphur oxides inside the hot gases. The sensor provides a light source 9 which is preferably a broad-band light source, a waveguide element 10, an optical element 11 which is wavelength selective, and a mirror 12. All components inside the little chamber 5 are of temperature resistance material and fabricated by shear flow crystallization at least the optical element 11 as described below.

Since the optical element 11 and the mirror 12 are placed inside the little chamber 5 by a distance of the so called absorption length 14, a light beam which emanates from the light source 9 and passes through the waveguide element 10, the optical filter element 11, to the mirror 12, at which the light beam will be reflected mainly and is redirected through the optical components 11 and 10 until entering a detector 13 which is provided like the light source 9 outside the little chamber 5, traverses the absorption length 14 twice. In the presence of absorbing particles like atoms and/molecules inside the little chamber 5, the light beam of the light source will be attenuated, which is detected by the detector 13. The amount of attenuation can be related to special combustion parameters which are well known for a man who is skilled in the art. To ensure that parts of hot gases enter the little chamber 5 through the porous membrane 7, inside the little chamber 5 less pressure P1 is applied than the combustion pressure P2 inside the combustion chamber 2.

A main advantage of the inventive optical sensor is its temperature resistance which allows measuring very close to the combustion process to get pristine burner information. The basis of the temperature resistance is the way of production of preferably all sensor elements, at least of the optical element, by means of shear flow crystallization. The optical element 11 can be built as a single filter element or a filter bank, as described with reference to the embodiment in FIGS. 15 and 16.

So in a preferred embodiment of the inventive optical sensor, means for wave guiding is provided at least between the light source and the optical element for guiding light from the light source to the optical element and/or for guiding reflected light from the optical element to a detector which is made also by shear flow crystallization.

The necessity to optimize combustion operations, monitor the combustion processes to avoid instabilities and their severe consequences explain the growth of interest in combustion control. Filtered Rayleigh scattering (FRS) is a new class of laser diagnostics permitting the measurement of single and multiple properties simultaneously; see G. S. Elliott et al., Measurement Science and Technology, 2001, 12, 452-466, and D. Most and A. Leipertz, Applied Optics, 2001, 40, 5379-5387. The FRS method employs a molecular iodine filter in conjunction with an injection-seeded, frequency doubled Nd:YAG laser. In this technique, the different spectral broadening of the particle Mie and molecular Rayleigh scattering is used, to separate these two contributions by blocking out the Mie signal with an appropriate ultra-thin molecular absorption filter, usually using the molecular absorption line of iodine. The laser frequency can be tuned to transitions of iodine at 18 788 cm$^{-1}$. Comparison of measured signals with theoretical transmission (including Doppler shift and broadening) allows for the measurement of the average velocity, density, temperature and pressure.

Solid material with absorbed non-bonded molecular iodide could be used as the ultra-thin notch filter. But attempts to absorb molecular iodine in a solid matrix usually lead to breakage of the I—I bond and formation of the bond matrix-I. For example, the formation of ad-layers on the reconstructed surfaces of Si(111) and Ge(111) leads to formation of Si—I and correspondingly Ge—I bonds, though with the conservation of strong I—I interaction. For Ge(100) the formation of a layer of molecular iodine on the top of iodine atoms, connected to the Ge(100) (2×2)(c(2×2) surface, was reported. The sorption of iodine by fully $Cd^{2+}$-exchanged zeolite X results in disproportion and formation of cyclo-$I_4$ and cyclo-$I_5$ products. Especially interesting are results on absorption of iodine by mesoporous materials. In iodine-doping complexes of activated carbon fibers (ACF) consisting of a three-dimensional disordered network of nano-graphites with a mean in-plane size of about 30 Å with many neutral $I_2$ molecules present in micropores, the charge-transfer rate is about 0.008. For the intercalation of $I_2$ by nanographite (each nanoparticle of the size 7-8 nm made of 3-7 graphene sheet has a polyhedral shape with a hollow inside) was also reported to have a weak degree charge-transfer of 0.024 (Raman spectra). Products of reversible intercalation of $I_2$ by single-walled nanotubes (SWNT) exhibit a moderate charge transfer of 0.018, which could mean formation of $I_3^-$ and $I_5^-$ in interstitial channels of a SWNT bundle. For double-walled carbon nanotubes (DWNT), poly-iodine anions and the charge transfer between iodine and DWNT were also identified. This means that carbon nanotubes, ACFs and nanographite have similar affinity to iodine.

The inventive optical sensor benefits from a method for fabrication and use of nano- or microcrystalline metal-, metal oxide, or other inorganic nano- or microparticles arrays for sensors in gas turbines or combustors, for example for the analysis of burner gas composition locally, near to the burner (temperature, pressure, $NO_x$ pollutant emissions, CO emissions, unburned hydrocarbons, volatile organic compounds, nitrous oxides, sulphur oxides). Such sensor systems allow for the immediate monitoring of combustion process.

One aspect of the inventive optical sensor stems from a method of obtaining two-dimensional arrays (secondary arrays) built of aligned parallel or a more complicated geometrical pattern, built of one-dimensional arrays (microfibers), which consist of metal oxide, metal, or other inorganic nanoparticles, deposited onto an amorphous, polycrystalline or single crystal support. Using shear-flow crystallization of nanoparticles with subsequent coalescence of the particles by external treatment, e.g., by heat treatment, it is also possible to assemble one-, two-, or three-dimensional nano- or microcrystalline arrays with the gradient of microstructure and electron/hat transport properties along the arrays or articles, built of these arrays.

In addition to producing the wavelength selective optical element by shear-flow crystallization, it is also possible to obtain a multilayer mirror using the same technology, built of grated overcoated surfaces with a matching multilayer structure, which reflects within the wavelength around the Bragg peaks, with reflectivity, tunable by changing the angle of incidence. Also mirrors with very broad bandwidth, so called supermirrors, can be obtained by depositing multilayers of two-dimensionally micro- or nanoordered arrays with different periods, one for each desired wavelength band. The main limit is absorption. Depending on process parameters, multilayers are also obtainable which reflect only within a range around the Bragg peak with reflectivity in λ, which can be tuned by changing of angle of incidence. Two-dimensional arrays of aligned nanotubes, doped or not doped with molecular iodine, which could be used for waveguiding or for the design of solid-state ultra-thin notch filter systems for application in Filtered Rayleigh scattering laser diagnostics of combustion operations, are also possible to produce by using shear flow crystallization.

Finally, means for waveguiding by creation of one-dimensional or two-dimensional arrays possessing diffraction index contrast across the array for waveguides are obtainable with the aforementioned technique. So the inventive optical sensor device, which preferably provides a light source, means for waveguiding, an optical wavelength selective filter element, a mirror, and finally a light detector, can include main components produced by shear flow crystallization.

Description of the experimental procedure of fabrication of some particular $SiO_2$ nanoarrays can be found in V. Shklover, Chemistry of Materials, 2005, 17, 608-614. The gaskets for the packing cell were constructed from micro slides (Superiors, Marienfeld, Germany) and Mylar film with a thickness of 25 µm (Fralock Div. Lockwood Ind. Inc., 21054 Osborne St., Canoga Park, Calif. 91304, USA). All the gasket elements were carefully cleaned. The first of three non-lithographic methods discussed in Y. Lu et al., Langmuir, 2001, 17, 6344-5350, of the generation of the channel structure was applied, namely, the use of a piece of soft paper to wipe the surface of the Mylar film. For the crystallization of the colloids, the sonicator Branson 1510 was used (Bransonic®) operating at a frequency of 42 kHz, maximum power 80 W, RF-power 80 W. The fabrication process was continued with interruptions for about five days. The controlled drying of the samples was done at 90° C. and 60° C. after assembling was accomplished.

For detection purposes of the processed layers, a scanning electron microscopy (SEM) LEO 1530 microscope with software LEO 32 V02.03 was used (LEO Elektronenmikroskopie GmbH), accelerating voltage was 3 kV, in-lens detector, the samples were coated with 3 nm Au to avoid charging problems. Further, a transmission electron microscopy (TEM), Tecnai $G^2$ F30 microscope with ultra high atomic resolution was used (FEI Company, Eindhoven, The Netherlands), operating at accelerating voltage of 300 kV. The $SiO_2$ particles for check of their amorphous character were prepared and the nano-crystalline arrays (NCA3) crystals were powderized in a mixture of ethanol and acetone and were brought onto the Cu grid, coated with carbon film (Plane GmbH, D-35578 Germany).

Optical microscopy. Leica MZ 16 optical microscope in both transmission and reflection modes with software IM 1000 (Leica Microsystems) was used.

X-ray powder diffraction. Mar300 imaging-plate detector system (Marresearch GmbH, 1999), equipped with a housemade furnace, was used for powder diffraction measurements. In this design, the original base of the Mar300 was modified to allow the additional translation along the spindle axis to accommodate the furnace. The furnace consists of a housing of stainless steel with integrated water cooling, X-ray entry and exit windows (Kapton), and a window for in situ observation of the specimen by external CCD-camera. The furnace is filled with helium to provide an inert atmosphere and good thermal stability. Calibration of the furnace in the range from RT to 900° C. was performed before the measurements. The quartz-glass capillary of 0.5 mm diameter and 0.01 mm wall thickness was filled up to ca. 30 mm length with rod-like crystals and sealed in the air. The sample was rotated in the range of $\phi=0-180°$ during data collection, 1800 sec per exposition with $\lambda(MoK\alpha1)=0.7093$ Å (quartz monochromator), collimator diameter of 0.5 mm, and sample to detector distance of 200 mm. The measurement of a standard Si sample was measured for precise determination of the sample-to-detector distance and x,y-pixel coordinates of the direct beam. The measurements at 20, 200, 400, 500, 550, 600, 700, 750, 800, 850, 900, 950 (20 successive measurements were performed at this temperature 950° C.), 800, 500, 20° C. were performed, the heating/cooling rate was 10° C./min, the holding time at each predetermined temperature was equal to the duration of the X-ray exposition (30 min). All the X-ray experiments on Mar300 were performed using the mar345(dtb) software package (Marresearch GmbH, 2003), the conversion of X-ray results from 2D to 1D data was done with FIT2D software, published by A. P. Hammersley as FIT2D V10.3 Reference Manual V4.0, ESRF98HA01T, ESRF, Aug. 26, 1998. The STOE automated powder diffractometer system was used to check the phase composition of the sample NCA3, formed in the "cold" part of the capillary, filled with NCA2, during the annealing (Debye-Scherrer scan mode, CuKα, Ge(111) monochromator, a linear position sensitive detector).

Figure 2:
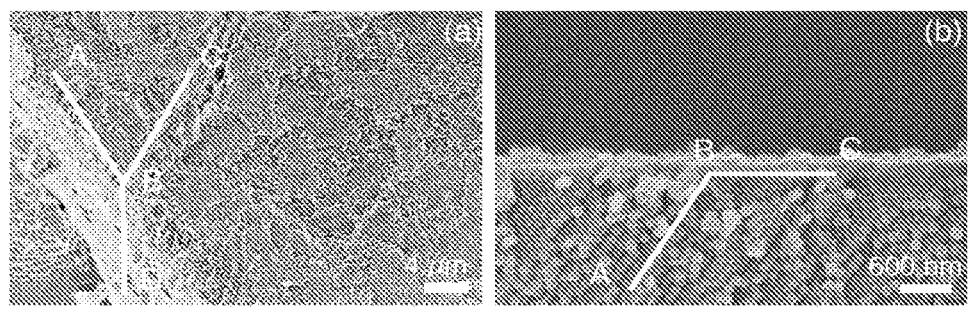
FIG. 2 Patterns, showing structures NCA1 and NCA2.

The shear-flow assembling method described in, e.g., papers by Y. Xia et al., Adv. Mater. 2000, 12, 693-713, and Aust. J. Chem., 2001, 54, 287-290, combining hydrodynamic flow and physical confinement, was used for assembling nanocolloidal arrays. The shear-flow crystallization is a convenient assembling method, but its understanding requires the account of several complex processes: (a) sedimentation in a gravitational field, (b) hydrodynamic shear-flow with very small gradient of velocities G ($G=2v_m r/R^2$, $v_m$ is maximum velocity, r and R are radii of particle and channel), (c) Brownian motion and particles diffusion, (d) local fluctuations caused by ultrasonic sound waves radiation (~42 kHz, output 0.15 W cm$^{-2}$), and (e) capillary stresses (which can lead to cracking the film during the drying). To ensure the use of a shear-flow method, a reference experiment was performed on assembling spherical 255 nm Seradyn colloidal polystyrene (PS) nanoparticles into ordered 3D nanocrystalline arrays NCA1. Then, 80 nm Klebosol® colloidal silica particles were assembled into NCA2 colloidal crystals. The thickness of NCA1 and NCA2 of 25 μm was controlled by the thickness of the Mylar film used. Scanning electron microscopy was used for the characterization of the obtained crystalline arrays NCA1 and NCA2. FIG. 2 hereto shows SEM patterns of structures NCA1 and NCA2. FIG. 2a shows a projection of the structure NCA1, showing termination of the crystal by the faces {111} (plane ABC) and {110} (plane ABD). The crack parallel to one of the faces {110} could be also seen (plane CBD). FIG. 2b shows projection of the structure NCA2. The rational crystallographic orientation of the termination face {110} could be seen. The examination of the SEM patterns clearly indicates . . . ABC . . . stacking sequence of PS or correspondingly silica particles and fcc structure of NCA1 and NCA2 (space group Fm3m, packing density 74.05%), observed in many colloidal crystals. The structures of the NCA1 and especially NCA2, which is built of the less monodisperse $SiO_2$ nanoparticles, therefore have many defects. Disordered structure of nanoarrays seems to be problematic for device fabrication for, e.g., photonic or microelectronic. The rational crystallographic orientation of the faces and major cracks of the resulted NCA1 and NCA2 draws attention to FIG. 2.

The observed character of growth of nanocrystalline arrays is the result of a combination of a preferential growth mechanism of the primary nanocrystallites (small arrays formed by several primary nanoparticles) and geometrical constraints imposed on the nanocrystallites by cell geometry. The observed orientation of one of the crystallographic directions of resulting colloidal arrays NCA1 and NCA2 is along the shear directions, and a second one is parallel to the template surfaces, FIGS. 3a and b. This means that the shear flow direction (at small gradient of velocities) and template geometry can be used for the control of the film crystallography, which is beneficial for practical applications.

Figure 3:
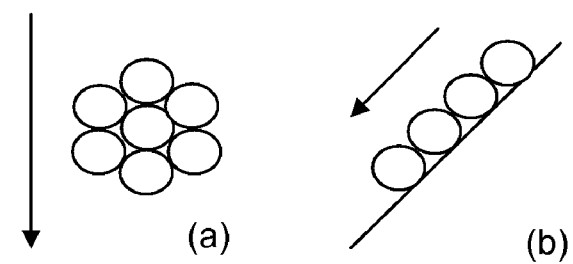
FIG. 3 Preferential crystallographic orientation of colloidal arrays, imposed by the growth conditions.

Preferential crystallographic orientation of colloidal arrays, imposed by the growth conditions, is shown in FIGS. 3a and 3b. One of the crystallographic directions of the nanoarray of spherical particles is oriented preferentially along the shear directions as indicated in FIG. 3a. Template geometry dictates crystallographic orientation of the external top and bottom faces of the nanoarray parallel to the substrate is shown in FIG. 3b. Arrows indicate direction of the shear flow, which is very slow and comparable to the sedimentation rate. The possibility of kinetically controlling the crystallographic orientation of the nanoarray is beneficial for practical applications.

The parallel assembling of nanowires (NW) and nanotubes (NT) on the chemically patterned substrates is another example of the combined use of fluidic alignment (shear flow) for hierarchical assembly of 1D nanomaterials into a functional network of controlled periodicity of the several μm-size. The dependence of the NW angular distribution on the shear-flow rate was also established.

Figure 4:
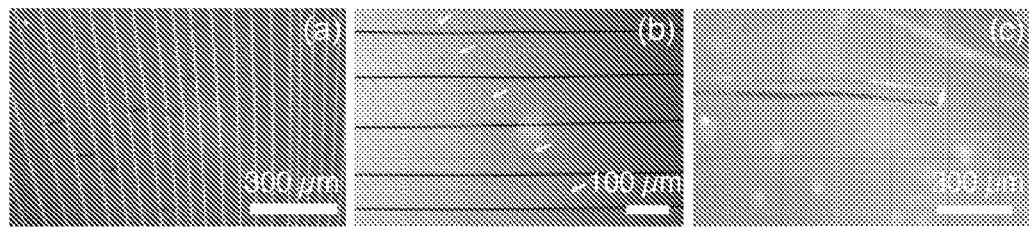
FIG. 4 Optical photograph, showing microfiber morphology of the NCA2 after drying, FIG. 5 Possible geometries of two-dimensional microcrystalline arrays, FIG. 6 Schematic illustrating location of carbon nanotubes inside of the channels in NCA1, FIG. 7 Possible gratings built of patterned arrays of nanocrystalline building blocks, FIG. 8 Schematic of possible geometry of article for one of the optical applications, FIG. 9 Optical photographs, showing three different zones in the quartz capillary, FIG. 10 Evolution of X-ray diffraction pattern of the colloidal array NCA2 as a function of temperature in high-temperature zone, FIG. 11 SEM patterns, illustrating change of the structure of the partially transparent crystal NCA3, FIG. 12 TEM patterns taken from powderized crystals NCA3, FIG. 13 SEM patterns of the crystals NCA4, consisting of the mixture of β-crystobalite and tridimite, FIG. 14 Transmission spectrum of NCA1, FIG. 15 Schematic of remotely operated filter-bank and FIG. 16 Detailed section view of a filter-bank.

The drying leads to very characteristic microfiber morphology of the resulting NCA2, with the microfibers directions approximately parallel to the shear in the homogeneous part of the film, microfibers width ranging from 50 to 200 μm and microfibers length up to 1 cm, illustrated in FIG. 4. In FIG. 4, optical photographs show microfiber morphology of the NCA2 after drying. FIG. 4a shows a photograph, recorded in reflectance mode; FIG. 4b shows a photograph, recorded in transmission mode. The arrows indicate one of the pattern lines on the surface of NCA2 across the microfiber, confirming the appearance of the microfiber morphology due to drying. The observed line pattern on the microfiber surface could result from the oblique orientation of the packing cell during the crystallization. FIG. 4c shows an isolated microfiber, built of colloidal NCA2 with remarkable mechanical stability.

A possible mechanism of cracking of primary 2D arrays, by high capillary stresses and counteracting adherence to substrate, was described by D. Bellet and L. Canham in Advanced Materials, 1998, 19, 487-490. The suggested methods of drying to avoid cracking comprise supercritical drying, drying with solvent of smaller surface tension, freeze-drying, or slow evaporation. The formation of the microfibers during the drying process and not during the crystallization could be proved by detailed observation of the lines pattern on the microfibers surfaces, FIG. 4b. The NCA2 microfibers have remarkable mechanical stability. The microfibers in the central, most homogeneous part of the NCA2 can be approximately characterized by dimensions of 25×150×10000 μm. Of course, the 1D nanoarrays (wires or fibers) can also be used as mats (both supporting and free-standing), but the observed controlled assembling of arrays with predicable crystallographic orientation brings many benefits; the nano- or microcrystalline planar patterns (films) could find more practical applications in optics and microelectronics than correspondingly not oriented 2D or 3D bulk structures. The perfect alignment of the 1D nano- or microarrays into planar high-density patterns is one of the challenges of nanotechnology.

Figure 5:
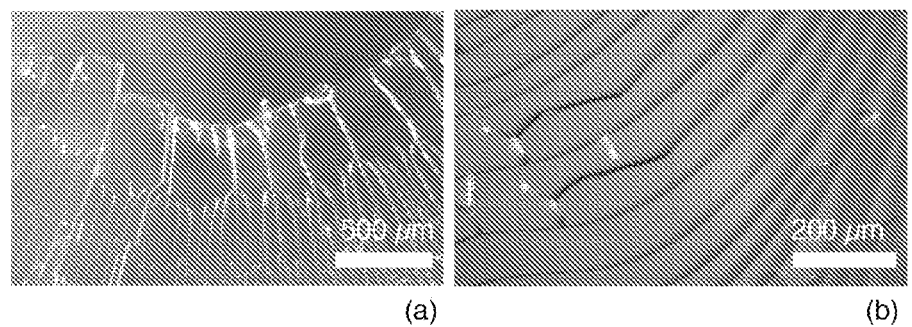

FIGS. 5a and b show possible geometries of two-dimensional microcrystalline arrays. The structure shown in FIG. 5a, consisting of parallel nearly equidistant planes, stabilized by corresponding annealing and sintering, could find application as integral components for VUV and soft X-rays optics, like monolayer and multilayer mirrors, plane and focusing gratings for focusing and monochromatization. The tunable parameters are: particles materials, particles diameter, gratings width, thickness, separations between the gratings, substrate material, and substrate curvature. The possible substrate materials are: LiF, $MgF_2$, $CaF_2$, $BaF_2$, $Al_2O_3$, and quartz. Also non-uniformly spaced grooves can be used, especially variable-line spacings (VLS) gratings, see review by H. A. Padmore et al. in Vacuum Ultraviolet Spectroscopy II., Eds. J. A. Samson and D. L. Ederer. Academic Press, 1998. pp. 21-72.

Figure 6:
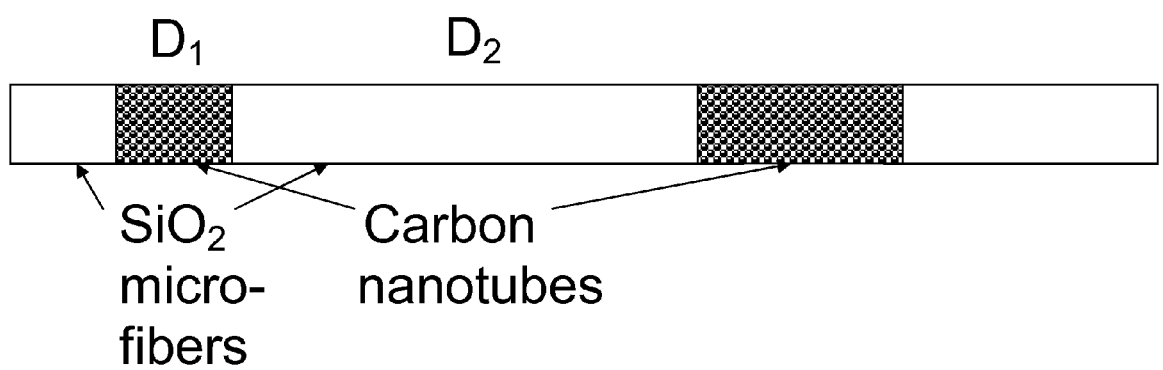

The microfiber structures shown in FIG. 6 can also find applications as a templated surface for aligning of carbon nanotubes via self-assembling for application in field-emission displays and other microelectronic devices. The advantages of carbon nanotubes (CNT) as field-emission materials for displays and other vacuum microelectronic devices include a low-threshold field for emission and sustainable high-emission current. Currently used CVD deposition at high temperatures>800° C. and a reactive environment restrict application of CNT for devices with limited thermal and chemical stability, e.g., field-emission displays (FED). The disadvantage of screen-printing, one of the alternative approaches, is low resolution and inefficient use of materials. The channels width of 2-10 μm and separations between the channels, observed in the NCA1, can be compared to a self-assembled structure. The schematic illustration in FIG. 6 shows locations of carbon nanotubes inside of the channels in NCA1 (cross-section view). The shear-flow method can be used for alignment of carbon nanotubes in the channels between $SiO_2$ microfibers. The values are of $D_1 \approx 2$–$10$ μm, $D_2 \approx 50$–$200$ μm.

Figure 7:
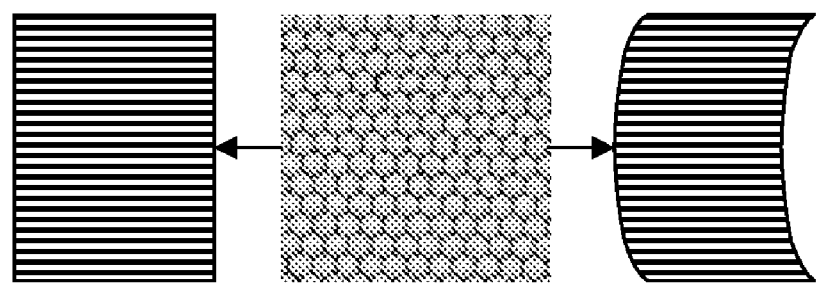

The suggested "steric" assembling in FIG. 7 does not need pre-treatment of a substrate for production of alternating hydrophobic and hydrophilic regions. The resulted pre-patterned structure can be used, on the next step of nanostructure fabrication using self-assembling, for fabrication of 2D arrays of carbon nanotubes aligned within the channels between the microfibers. The aligned carbon nanotubes arrays can be used for waveguiding or, for example, after absorption of molecular iodine, for design of ultra-thin notch filter systems in Filtered Rayleigh scattering (FRS), which is new class of laser diagnostics with important applications in optimization of combustion operation in gas turbines.

Figure 8:
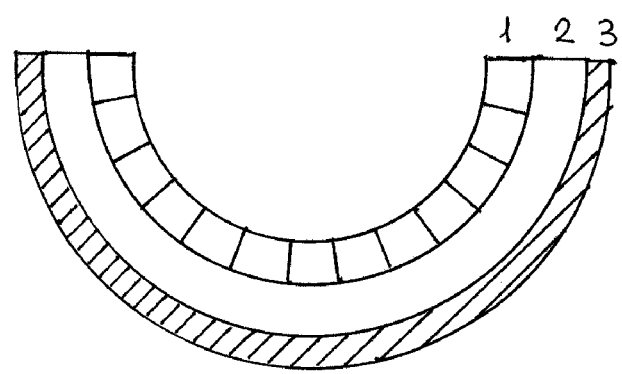

In order to check the sintering behavior of NCA2, the in situ X-ray study of the crystals NCA2 was carried out, placed into the quartz capillary having a diameter of 0.5 mm and length of ca. 30 mm. A X-ray image plate scanner MAR300, equipped with the high-temperature furnace, was used. Three different zones can be distinguished in the capillary after the heating, see FIG. 7. Possible gratings can be built of patterned arrays of nanocrystalline building blocks like in FIG. 4a. The left and right portions of FIG. 7 show plane and focusing gratings, respectively; the middle portion of FIG. 7 shows a nanocrystalline moiety, constituting, e.g., black lines on the left and right portions of FIG. 7. The phase changes were checked in situ in the small part of the capillary, which remained in the X-ray beam during the measurements (X-ray spot size of 0.5 mm). Thee structure transformations of NCA2 during annealing can be observed, see FIG. 8, which shows a schematic of possible geometry of an article for one of the optical applications obtained by shear-flow crystallization of nanocolloids and subsequent heat-treatment curvature two-dimensional array, consisting of parallel aligned one-dimensional micro-or nanoarrays with crystallographically rational faces and controlled thickness (cross-sections of arrays are shown). One of the applications could be windowed photoemissive photodiodes.

The colloidal $SiO_2$ structure NCA2 transforms into cubic β-cristobalite (Fd3m, $D_x=2.186$ g $cm^{-3}$) between 750° C. and 800° C. As a result of continuous heating at 950° C. during 12 h, the β-cristobalite transforms into a mixture of coexisting β-cristobalite (major phase) and hexagonal β-tridymite ($P6_3$/mmc, $D_x=2.244$ g $cm^{-3}$). Cooling to room temperature leads to formation of product, containing β-cristobalite, β-tridymite (major phases), and low quartz. According to ex situ X-ray study, performed ca. seven days after heating, the middle zone NCA4 contains a mixture of tetragonal β-cristobalite ($P4_32_12$, $D_x=2.350$ g $cm^{-3}$) and monoclininc α-tridimite (Cc, $D_x=2.269$ g $cm^{-3}$).

Formation of high-temperature polymorphic modification of $SiO_2$ cubic β-cristobalite at 750-800° C. during annealing of colloidal crystal NCA1 draws attention. According to the generally accepted view of silica phase changes, the α-cristobalite is the stable form at room temperature. But the presence of β-cristobalite after heat treatment was observed in many other studies, see, for example, M. A. Butler et al., J. Appl. Cryst. 1997, 30, 467-475. The transition between β- and β-cristobalite is strongly discontinuous and precise transition temperature can be altered by the presence of defects, like stacking faults, chemical impurities and there is a hysteresis in the measured value of $T_{tr}$ on heating and cooling.

The β-cristobalite is more disordered than α-cristobalite and its presence in the product of annealing of a colloidal nanocrystalline array immediately after heating could be very characteristic. Different models were developed to explain the disordered structure of β-cristobalite, which has to possess unrealistic Si—O—Si bond angles of 180° and Si—O bond lengths of 1.51 Å. A correlation between the domain theories of disorder nature or dynamic theories and those observed in the present study's formation of β-cristobalite from nanocrystalline material is of interest.

Crystallization behavior and phase transitions using nanopowders may not follow the traditional phase transition routes. For example, depending on synthesis route, nanocrystalline $ZrO_2$ starts to transform to the high-temperature stable tetragonal polymorph at essentially different temperatures: at ca. 1200° C. for monoclinic crystalline $ZrO_2$ powder (size of cube-shaped crystallite ca. 14 nm) produced by forced hydrolysis, at. ca. 400° C. for X-ray amorphous microspheres obtained by mixed-solvent precipitation, and at ca. 600° C. for X-ray amorphous powder, obtained by alkoxide hydrolysis and condensation. The formation of tetragonal zirconia is probably related to the presence of amorphous zirconia because of their structural similarity, leading to possibility of topotactical crystallization on nuclei of amorphous zirconia as a mechanism of crystallization of tetragonal zirconia. This special feature of nanocrystalline materials forms the basis of improvement of stability of thermally grown oxide by nano-controlling, reported in a patent application by V. Shklover, et al., published as International Application WO 03/068673.

Figure 9:
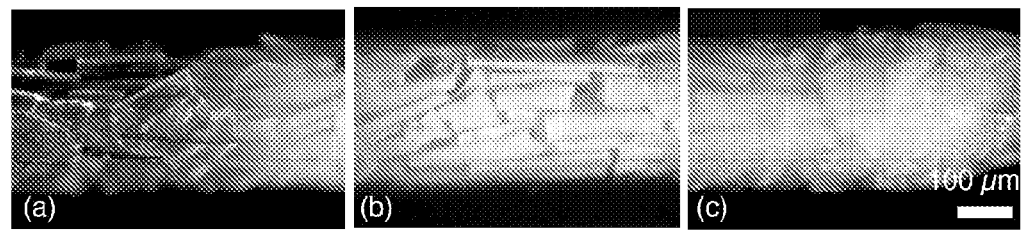

Three kinds of structures within one NCA3 crystal located between the heated and not heated zones can be observed having different degree of coalescence. FIG. 9 show optical photographs thereof, showing three different zones in the quartz capillary, filled with microfiber colloidal crystals NCA2 and heated during in-situ X-ray measurements. FIG. 9a shows crystals NCA3 in a low-temperature zone have a transparency gradient along the crystal length with an opaque part of the crystal in the right heated part. FIG. 9b shows opaque crystals NCA4 in medium-temperature zone and FIG. 9c shows opaque crystals NCA5 and products NCA6 of heating in high-temperature zone (smaller particles). The X-ray spot size 0.5 mm was focused on this part of the capillary during the in situ X-ray study. The capillary has a diameter of 0.5 mm, and a wall thickness of 0.01 mm. The degree of ordering and porosity decreases when going from the "cold" to "hot" part of the NCA3 crystal. Remarkably, the structure NCA3 remains amorphous after the coalescence, according to the TEM data, FIG. 9c. Indeed, the Fast Fourier Transform (FFT) of the image on FIG. 9c shows weak diffraction spots of only photonic NCA3 crystal (its "cold" part), but not diffraction due to crystallinity of NCA3 grains. Diffusion of atoms on the cluster surface towards regions of lower curvature (less strongly bound to the neighboring atoms) was considered as a driving force of coalescence of crystalline nanoparticles. It is possible, that coalescence of amorphous nanoparticles of NCA2 proceeds along other mechanisms, including first crystallization stage. The formation of an essentially disordered β-cristobalite structure, as a first observable crystalline product of annealing of NCA2, confirms this suggestion.

Figure 10:
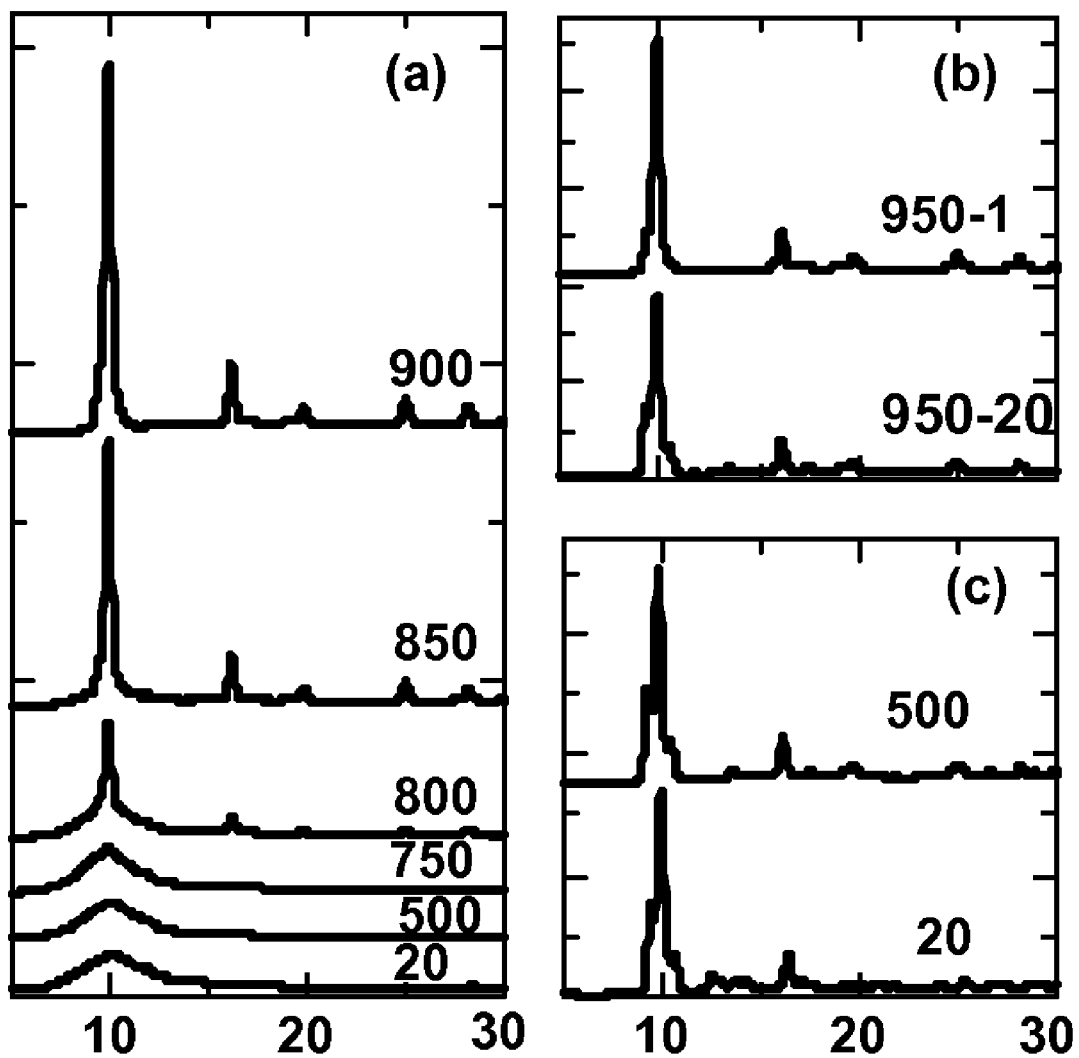

FIGS. 10a, b, and c show an evolution of X-ray diffraction pattern of the colloidal array NCA2 as a function of temperature in a high-temperature zone. Duration of every X-ray measurement at constant temperature was 30 min, heating or cooling rate was 10° C./min, λ(MoKα1). Three structure transformations of CA2 during the annealing could be emphasized: (a) Heating-step—Formation of the β-crystobalite from $SiO_2$ colloids during the heating at 750-800° C.; (b) Isothermal annealing step—Formation of the mixture of coexisting cubic β-crystobalite (major phase) and hexagonal tridimite at prolonged isothermal heating at 950° C. during ca. 12 h (pattern 950-20); and (c) Cooling step—final product contains β-crystobalite, tridimite and low quartz.

Figure 11:
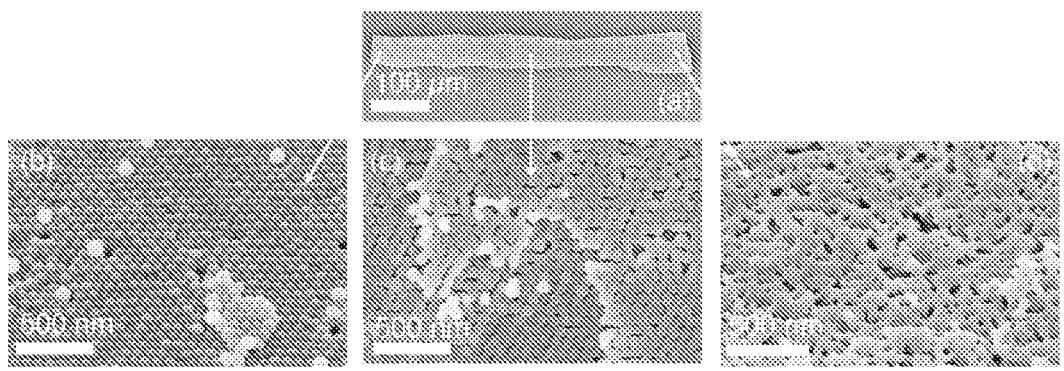

FIGS. 11a to d show SEM patterns, illustrating the change of the structure of the partially transparent crystal NCA3 as a function of the temperature gradient in the capillary during annealing. FIG. 11a show crystal NCA3 used for SEM measurements. All the SEM patterns b-d were recorded from this crystal. FIG. 11b shows disordered closest fcc packing in the initial NCA2 in the "cold" part of crystal NCA3. FIG. 11c shows a sintered structure in the middle part of crystal NCA3. The partial coalescence is observed, but the structure still exhibits ordering. FIG. 11d shows a sintered "hot" part of the crystal NCA3 with local markers of the ordering still present.

Structure NCA3, exhibiting partial coalescence in FIG. 11c, can be considered as a model system for considering of phonon properties of nanomaterials. Opto- and microelectronic devices, like laser sources, systems for energy conversion, and computers, may generate heat during their operation, but they have to remain within the very narrow temperature range to maintain the possibility of frequency control, which defines circuit life-time, meaning they need efficient heat-removal. On the contrary, current leads of high-$T_c$-superconductors have to have small heat conductivity and need a thermal (e.g., metal oxide) buffer for directional heat removal. Electronic devices, comprising nano- and/or organic (or biological) components, need especially careful heat management. Thermal conductivity of nanomaterials depends on both particle size and particles arrangement (nanoarrays) and may differ very much from corresponding bulk materials. It is known that phonon transport in nano- and microgram structures has to be reduced due to scattering at the grain boundaries. This is especially the case when grain size becomes comparable to the phonon mean free part (MFP) at a given temperature, which were approximately estimated as $l=5a(T_m/T)$, where a is the lattice constant, $T_m$ is the melting point, and T is the temperature. The dependence of phonon transport in sintered structures depends on the diameter and transparency of the interface. The necks become transparent for phonons, if the neck size becomes comparable to the grain size. The anisotropy of thermal conductivity κ equals approximately $$\frac{\kappa_\parallel}{\kappa_\perp} = \frac{S_\parallel d_\perp}{S_\perp d_\parallel},$$

where $$S_\parallel, S_\perp$$

are the neck areas, and $$d_\parallel, d_\perp$$

are the grain sizes in the directions along and normal to the structure plane. This is the situation we observe in NCA3, FIG. 12c. If the sintering leads to developing 1D-, 2D- or 3D-network of grains, connected through phonon-transparent necks, we can expect a structure with anisotropy of thermal conductivity of corresponding dimensionality. Arrays NCA4 and NCA5, built of crystals with grains size much larger than phonon MFP, can be considered as bulk materials, which concerns phonon transport properties.

Figure 12:
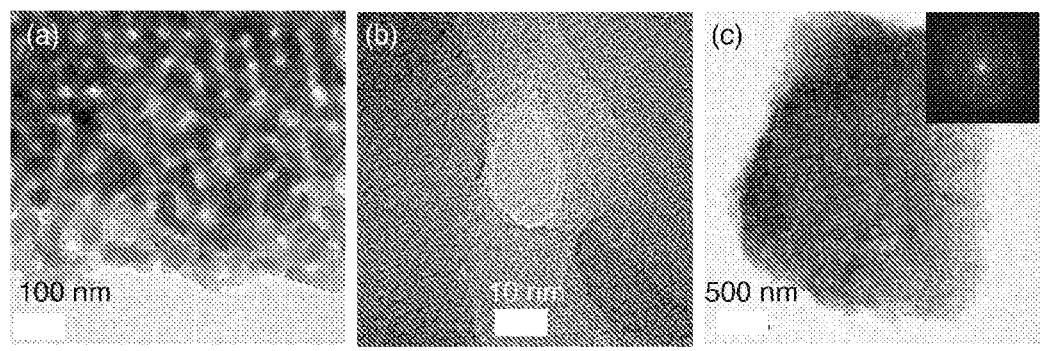

FIGS. 12a to c shows TEM patterns taken from powderized crystals NCA3. FIG. 12a show partially ordered structure in the middle part of the crystals NCA3. FIG. 12b show essentially amorphous structure of the particles and interface "necks" in the middle and "hot" parts of the crystal NCA3. The absence of crystallinity was checked also by recording diffraction patterns. FIG. 12c shows fragment of the NCA3 from the middle part. Diffraction due to only the photonic structure of NCA3 could be seen, with no diffraction due to crystallinity of $SiO_2$.

Figure 13:
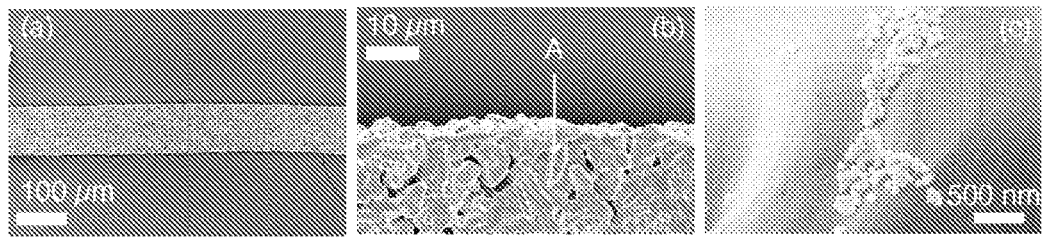

FIGS. 13a to c show SEM patterns of the crystals NCA4, consisting of the mixture of β-cristobalite and tridimite; FIGS. 13(a, b) show morphology of crystals, FIG. 13(c) shows nanocrystals of $SiO_2$, remaining on the surface of sintered μm-sized crystals after annealing. The microcrystalline microfibers NCA5 after complete coalescence of nanoparticles are very porous and retain perfect microfiber morphology, FIGS. 13a and 13b. The presence of not-transformed $SiO_2$ nanoparticles on the surface of μm-sized β-cristobalite crystals (FIG. 13c) after prolonged (around 12 h) heating may indicate the possibility of a phase transition from amorphous nanoparticles to crystalline nanoparticles at the first stage of annealing process with subsequent coalescence of small crystalline nanoparticles into μm-sized crystals.

Figure 14:
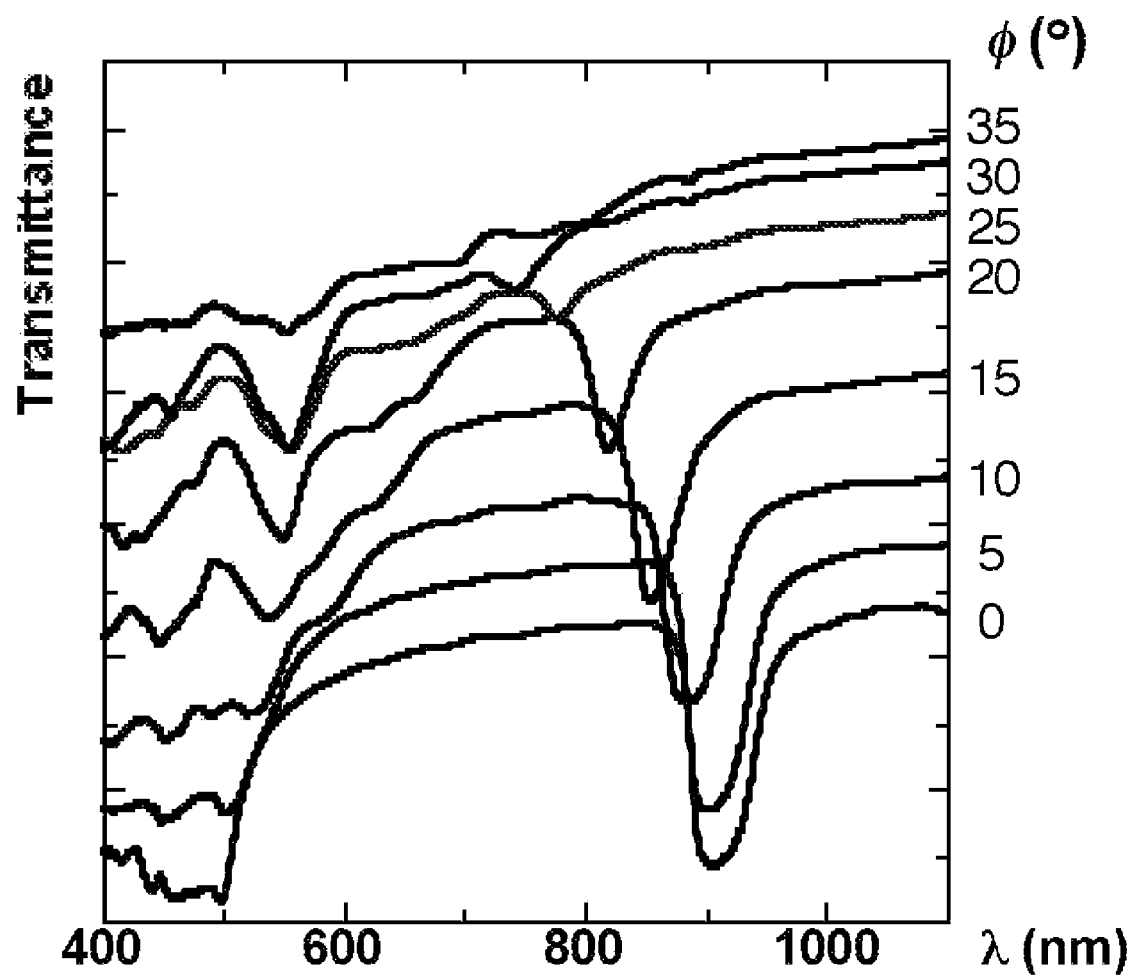

An example of the possibility of rejection/tuning of wavelength, e.g., by changing the angle between the incident beam and the normal to the surface of the filter, is shown in FIG. 14, which shows transmission spectra of NCA1 as a function of the angle φ between the primary monochromatic beam and normal to the NCA1 surface. The spectrum at (φ=35° was effected by the elements of cell design and can be excluded from discussion.

Figure 15:
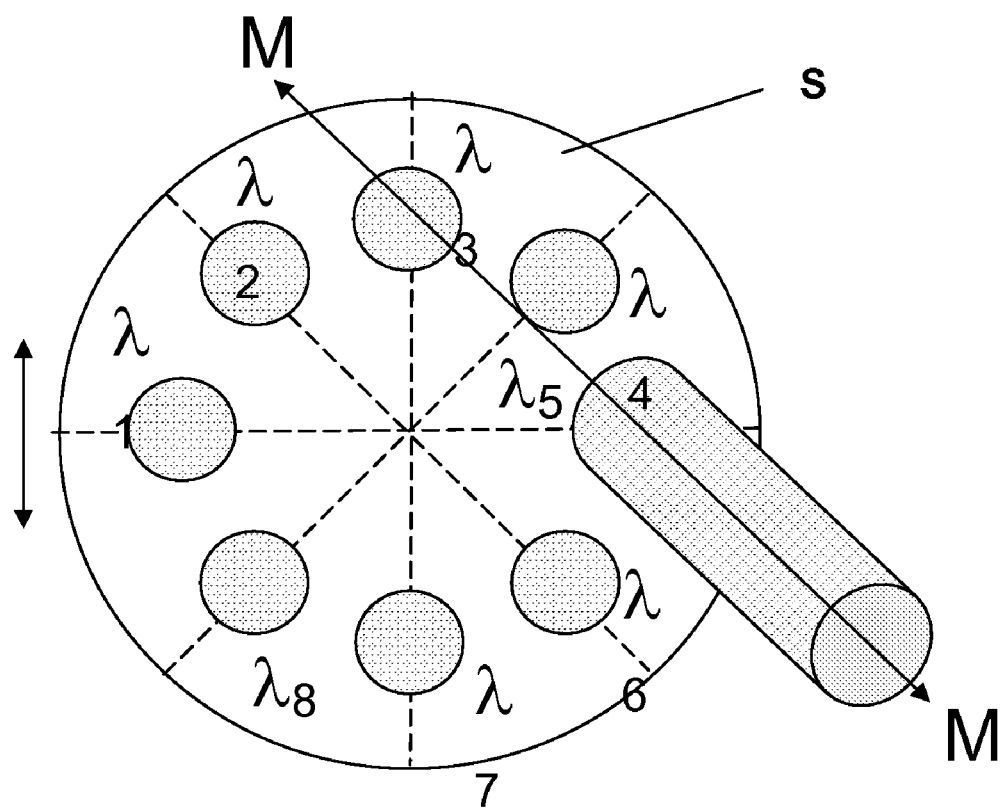

A schematic of a remotely operated filter-bank for positioning the appropriate filter ($\lambda_1$ to $\lambda_8$) of UV, visible, NIR, or IR spectra is illustrated in FIG. 15. M-M is the optical axis including the direction to the sensor opening in a gas turbine diagnostic system. Suggested fabrication methods as herein described for specific applications in gas turbine include: broad-band and narrow-band filters for suppression of absorption by molecules in distinct spectrum regions (UV, visible, IR), selective band photonic defect-induced band-pass filters, mesoporous framework structures for FRS supernarrow notch filters, molecular super-narrow-band notch filters based on, for example, molecular iodine encapsulated inside of mesoporous framework solids. Particularly promising for gas turbine diagnostics is the application of new nanoarrays in nanocrystalline photonic filters at high temperature ($T \leqq 600°$ C.).

Figure 16:
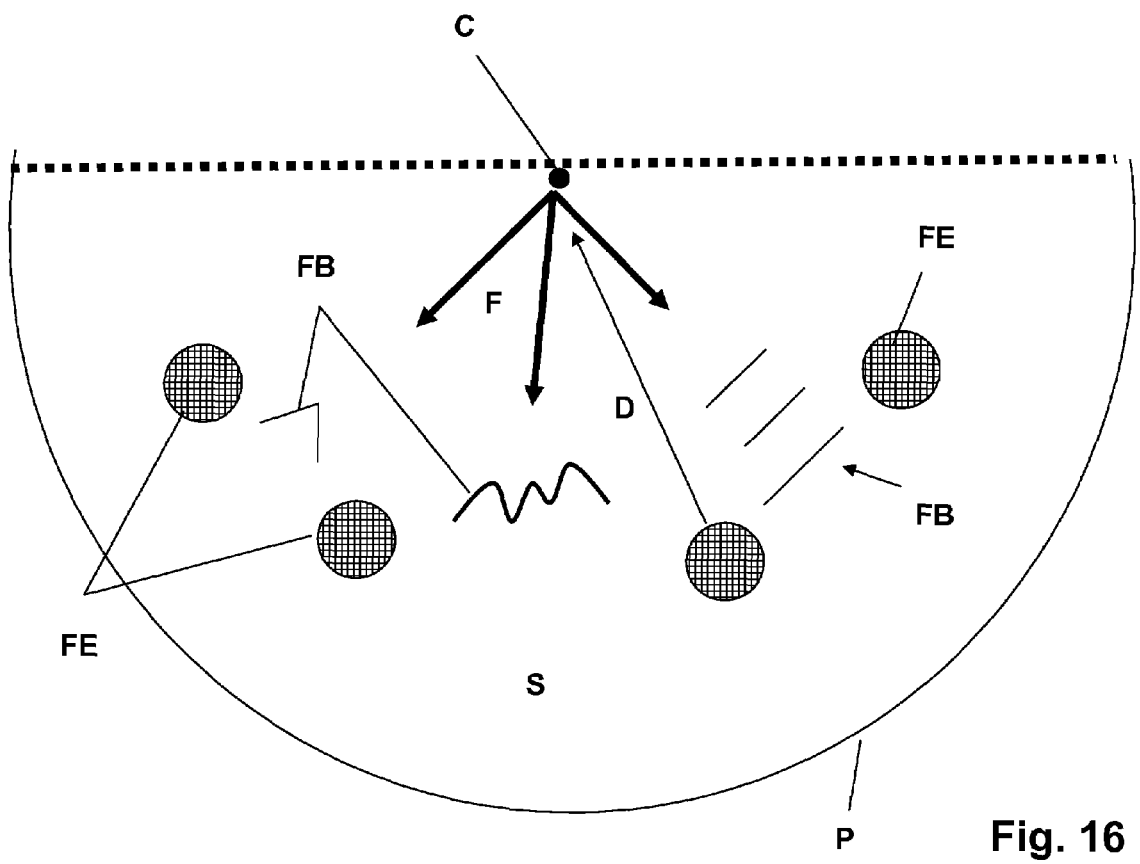

These kinds of different filter elements arranged all at one common substrate S are produced in one or several shear flow crystallisation processes using different flow conditions at each single filter element. To affect the flow conditions locally at each single filter location, individually shaped flow barriers FB are provided between two neighboring filter elements FE, as depicted in FIG. 16, showing a section of a disc shaped substrate. It is assumed that the flow F of metal colloids, while the shear flow step is directed from the centre C of the disc shaped substrate S, is radially outwards to its periphery P. Due to different shaped flow barriers FB, there will be different formation of colloidal particles accumulation and at least different deposition at the filter element regions. All the filter elements FE do provide the same distance D from the centre C of the substrate, which is advantageously for integration in a sensor element so that the substrate S together with the multitude of filter elements can be arranged rotatably about its centre axis. Doing this, different filter elements can be swung into the light beam if desired.

LIST OF REFERENCE SIGNS

1 Wall of combustion chamber
2 Combustion chamber
3 Hot Gas
4 Optical sensor
5 Little chamber
6 Opening
7 Selective porous membrane
8 Protection coating
9 Light source
10 Waveguide
11 Optical element
12 Mirror
13 Detector While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. An optical sensor device for local analysis of a combustion process in a combustor of a thermal power plant, the sensor comprising:
    at least one wavelength selective optical element configured and arranged to operate at temperatures up to 1600° C. and to be exposed directly or indirectly to hot combustion gases when produced by said combustion process, said optical element comprising an array of nano- and/or microcrystalline fibers created by shear flow crystallization;
    a mirror;
    a detector;
    a light source configured and arranged to emanate a light beam passing at least once through said at least one optical element and at least partially enters the detector;
    wherein said at least one optical element comprises at least two optical elements on the same substrate onto which each array of nano- and/or microcrystalline fibers are created by shear flow crystallization while rotating said substrate about an axis or rotation, and said at least two optical elements are positioned on said substrate at different circular sections towards said axis; and
    wherein said substrate is pivotably arranged about said axis of rotation so that the at least two optical elements are alignable one after the other to said light beam when emanating from said light source.

2. An optical sensor device according to claim 1, wherein:
    the mirror is arranged opposite to the light source relative to the optical element;
    the detector is positioned at the same side of the optical element as the light source; and
    the mirror includes a mirror surface from which said light beam can be at least partially reflected so that at least a reflected light beam fraction passes through said optical element in an opposite direction to be detected by the detector.

3. An optical sensor according to claim 2, wherein said mirror surface is planar or parabolic and spaced from said optical element.

4. An optical sensor according to claim 2, further comprising:
    means for waveguiding provided at least between said light source and said optical element, at least for guiding light from said light source to said optical element, reflected light from said optical element to the detector, or both.

5. An optical sensor according to claim 4, wherein said means for waveguiding is formed by shear flow crystallization.

6. An optical sensor according to claim 2, further comprising said combustor, and wherein at least said optical element and said mirror are positioned in said combustor.

7. An optical sensor according to claim 1, wherein said optical element is configured and arranged as a photonic filter-bank having a local maximum peak of photonic transmission.

8. An optical sensor according to claim 2, wherein the combustor includes a wall having an opening therein, the sensor further comprising:
    a measuring volume which borders the combustor wall, said measuring volume being encapsulated and communicating through the combustor wall opening with the combustor so that at least a portion of hot gases when in said combustor enters said measuring volume; and
    wherein at least said optical element and said mirror are positioned in said measuring volume.

9. An optical sensor according to claim 8, further comprising:
a high temperature resistant membrane which is selectively porous for chemical compounds, the membrane configured and arranged to cover said opening.

10. An optical sensor according to claim 1, wherein the combustor includes a burner flame, and wherein said optical sensor is positioned downstream of the combustor burner flame.

11. An optical sensor according to claim 1, wherein the sensor is configured and arranged to detect temperature, pressure, $NO_x$ pollutant emissions, CO emissions, unburned hydrocarbons, volatile organic compounds, nitrous oxides, sulphur oxides, and combinations thereof, inside said combustor.

12. An optical sensor according to claim 1, wherein said array of nano- and/or microcrystalline fibers of the optical element is of controllable dimensions, and comprises a primary array of colloidal organic, metal oxides, metal, or inorganic nanoparticles, deposited onto amorphous, polycrystalline, or a single crystalline flat or curvature support using shear-flow crystallization under distinct crystallization conditions and post-crystallization thermal treatment, the fibers including closely packed and distinct crystallographically rationally orientated crystal packing relative to external faces thereof and distinct orientation of the fibers relative to crystallization cell geometry.

13. An optical sensor according to claim 12, wherein the primary array of nano- and/or microcrystalline fibers are aligned.

14. An optical sensor according to claim 13, wherein the primary array of nano- and/or microcrystalline fibers is aligned parallel into two-dimensional secondary arrays.

15. An optical sensor according to claim 14, wherein the secondary arrays are configured and arranged to provide curvature gratings on at least one surface of said optical element for focusing and monochromatization of a light beam when passing through said optical element.

16. An optical sensor according to claim 15, wherein said at least one surface of said optical element is spherical, ellipsoidal, toroidal, paraboloidal, or cylindrical.

17. An optical sensor according to claim 14, wherein the secondary arrays are crystallized as a window that transmits a radiation of interest.

18. An optical sensor according to claim 14, wherein said secondary arrays of the optical element are aligned in multilayers with different periods, each period for a different wavelength band.

19. An optical sensor according to claim 14, wherein said secondary arrays comprise self aligned elements selected from the group consisting of nanotubes, nanorods, nanowires, and combinations thereof, onto a patterned optically transparent and high-temperature stable substrate.

20. An optical sensor according to claim 19, wherein the patterned substrate comprises channels for self alignment of said self aligned elements, having a channel width between 2 to 10 μm and being separated laterally by a distance between 50 to 200 μm.

21. An optical sensor according to claim 19, wherein said self aligned elements comprise molecular iodine or other molecular or atomic media exhibiting no substantial chemical interaction.

22. An optical sensor according to claim 13, made by a process further comprising: treating the primary array after crystallization, to create a gradient of coalescence of the particles and a resultant gradient of microstructure and electron/heat transport properties along the array.

23. An optical sensor according to claim 22, wherein treating the primary array after crystallization comprises external thermal treatment.

24. An optical sensor according to claim 1, wherein said at least two optical elements differ in properties of optical wavelength transmission.

25. An optical sensor according to claim 1, wherein said at least two optical elements are arranged equidistant from said axis of rotation.

26. A method of using an optical sensor, the method comprising:
providing an optical sensor comprising at least one wavelength selective optical element configured and arranged to operate at temperatures up to 1600° C. and to be exposed directly or indirectly to hot combustion gases when produced by said combustion process, said optical element comprising an array of nano- and/or microcrystalline fibers created by shear flow crystallization, a detector, a light source configured and arranged to emanate a light beam passing at least once through said at least one optical element and at least partially enters the detector, wherein said at least one optical element comprises at least two optical elements on the same substrate onto which each array of nano- and/or microcrystalline fibers are created by shear flow crystallization while rotating said substrate about an axis of rotation, and said at least two optical elements are positioned on said substrate at different circular sections towards said axis, and wherein said substrate is pivotably arranged about said axis of rotation so that the at least two optical elements are alignable one after the other to said light beam when emanating from said light source; and
passively filtering required parts of UV, visible, NIR, or IR spectra with said sensor, for actively qualitative and quantitative sensing change of gases inside a part of a gas turbine due to change in oxygen concentration and solid state conductivity inside portions of the sensor.

* * * * *